United States Patent [19]

Kerkenaar et al.

[11] Patent Number: 5,578,470
[45] Date of Patent: Nov. 26, 1996

[54] METHOD FOR PREPARING THIOL COMPOUNDS WITH BACTERIAL β-LYASE

[75] Inventors: Antonius Kerkenaar, Blaricum; Diederik J. M. Schmedding, Driebergen; Jan Berg, Nieuwegein, all of Netherlands

[73] Assignee: Nederlandse Organisatie Voor Toegepast, Netherlands

[21] Appl. No.: 232,357

[22] Filed: Apr. 22, 1994

Related U.S. Application Data

[63] Continuation of Ser. No. 863,978, Apr. 6, 1992, abandoned, which is a continuation-in-part of Ser. No. 148,418, Jan. 26, 1988, Pat. No. 5,182,194.

[30] Foreign Application Priority Data

Jan. 30, 1987 [NL] Netherlands ............................ 8700240

[51] Int. Cl.$^6$ ................................ C12P 11/00; C12P 7/26; C12N 9/88
[52] U.S. Cl. ...................... 435/130; 435/148; 435/132; 435/101; 435/74; 568/64; 562/507; 536/4.1
[58] Field of Search ..................................... 435/130, 101, 435/148, 74, 232, 280, 188; 562/507; 568/64; 536/4.1

[56] References Cited

U.S. PATENT DOCUMENTS

| | | | |
|---|---|---|---|
| 4,032,478 | 6/1977 | Lamparsky | 252/522 |
| 4,034,044 | 7/1977 | Sundt | 260/586 R |
| 4,328,311 | 5/1982 | Rowley | 435/188 |

FOREIGN PATENT DOCUMENTS

| | | |
|---|---|---|
| 974250 | 9/1975 | Canada . |
| 991084 | 6/1976 | Canada . |
| 999603 | 11/1976 | Canada . |

OTHER PUBLICATIONS

Bakke et al., "Mercapturic acid pathway metabolites of xenobiotics", Trends in Biochemical Sciences, Dec. 1984, pp. 517–521.
Kitazume et al., J. Chem. Soc., Chem. Commun. (1986), pp. 1331–1333.
Glass et al, J. of Lipid Research, vol. 23, pp. 352–356 1982.
Larsen et al. Molec. Pharma coli, vol. 29, pp. 97–103, 1986.
Larsen et al, Xenobiotica, vol. 13, pp. 689–700, 1983.
Lamoureaux et al. Pesticide Biochem. and Physiol., vol. 14, pp. 50–61, 1980.

Primary Examiner—Irene Marx
Attorney, Agent, or Firm—Webb Ziesenheim Bruening Logsdon Orkin & Hanson, P.C.

[57] ABSTRACT

A method for preparing thiol compounds, comprising: (1) reacting cysteine by a non-enzymatical addition reaction with a compound having the formula $(R_1)(R_2)C=C(R_3)$—$CO$—$R_4$ via an —S— bridge to form a cysteine conjugate, wherein the symbols $R_1$, $R_2$, $R_3$ and $R_4$ represent hydrogen or an optionally saturated and/or heterogeneous hydrocarbon group or wherein a combination of two groups selected from the group consisting of $R_1$, $R_3$ and $R_4$, together with the carbon atoms to which the groups are bonded, form an optionally saturated and/or heterogeneous hydrocarbon ring system of five or six members; and (2) reacting the cysteine conjugate so obtained in a concentration of >1 mM conjugate with a microbial β-lyase to form a thiol compound.

12 Claims, 7 Drawing Sheets

METHOD FOR PREPARING THIOL COMPOUNDS WITH BACTERIAL β-LYASE

REFERENCE TO A RELATED APPLICATION

This is a continuation of application Ser. No. 07/863,978 filed on Apr. 6, 1992 now abandoned which is a continuation-in-part of our U.S. patent application Ser. No. 07/148,418, filed on Jan. 26, 1988, now U.S. Pat. No. 5,182,194, which is incorporated by reference in its entirety.

BACKGROUND AND INTRODUCTION

The invention relates to a method for preparing thiol compounds.

In Lamoureux G. L. et al., Pesticide Biochemistry and Physiology 14, pages 50–61 (1980) the in vitro metabolism of pentachloronitrobenzene (PCNB) into pentachloromethylthiobenzene (PCTA) by means of an enzyme system obtained from onions is described. More particularly, this reference relates to the in vitro preparation of PCTA from PCNB at a pH of 7.9 by means of an enzyme system which contains dithiothreitol, glutathione and S-adenosylmethionine. The enzyme system was prepared from onion roots by ammonium sulphate fractionation and differential centrifugation. The enzyme system contained glutathione-S transferase activity with PCNB, C—S-lyase activity (also termed β-lyase activity) with S-(pentachlorophenyl)cysteine, S-adenosylmethioninemethyl transferase activity with pentachlorothiophenol (PCTP), and probably a few other peptidase activities. The yield of the thiol compound concerned, namely pentachlorothiophenol (PCTP) is, however, negligible in this method compared with the yield of PCTA (see page 55, right-hand column, lines 10–13 from bottom) so that this method is considered unsuitable for preparing thiol compounds on a commercial scale.

In Journal of Biological Chemistry, vol. 253, 24, pages 8854–8859 (1978), the cysteine conjugate β-lyase in rat liver is described. This enzyme catalysing cleavage of the thioether linkage in cysteine conjugates has been purified about 500-fold from rat liver cytosol. However, according to the chapter "Assay Methods" (page 8855), the thiol compounds obtained were directly methylated whereafter the methylated derivatives were identified by spectroscopy methods.

SUMMARY OF THE INVENTION

A method for preparing thiol compounds has now been found which comprises (1) reacting cysteine by a non-enzymatical addition reaction with a compound having the formula $(R_1)(R_2)C=C(R_3)$—CO—$R_4$ via an —S— bridge to form a cysteine conjugate, wherein the symbols $R_1$, $R_2$, $R_3$ and $R_4$ represent hydrogen or an optionally saturated and/or heterogeneous hydrocarbon group or wherein a combination of two groups selected from the group consisting of $R_1$, $R_3$ and $R_4$, together with the carbon atoms to which the groups are bonded, form an optionally saturated and/or heterogeneous hydrocarbon ring system of five or six members, (2) reacting the cysteine conjugate so obtained in a concentration of >1 mM conjugate with a microbial β-lyase to form a thiol compound and recovering the thiol compound prepared.

DETAILED DESCRIPTION OF THE INVENTION

Figure 1:
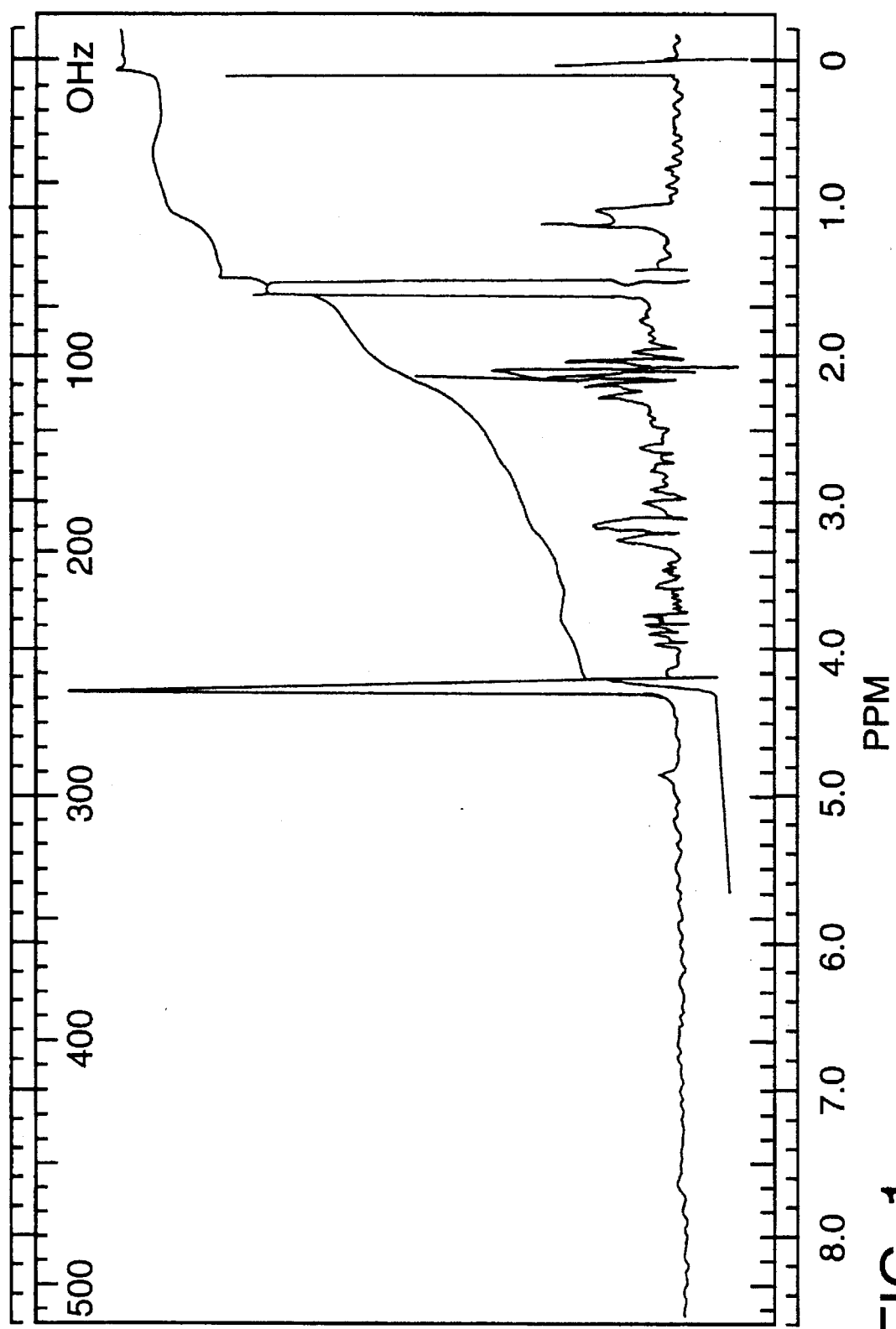
FIG. 1 shows the 90 $MH_z$ H-NMR spectrum of the product obtained in Example I.
Figure 2C:
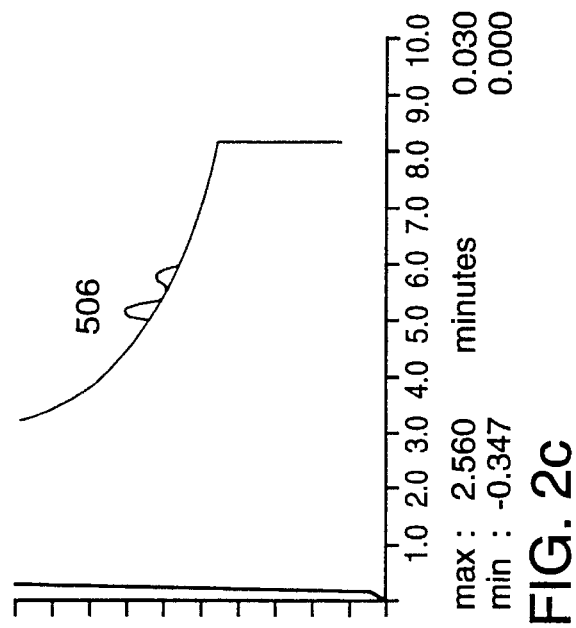
FIG. 2 shows gas chromatography analysis of the samples of Example I.
Figure 2B:
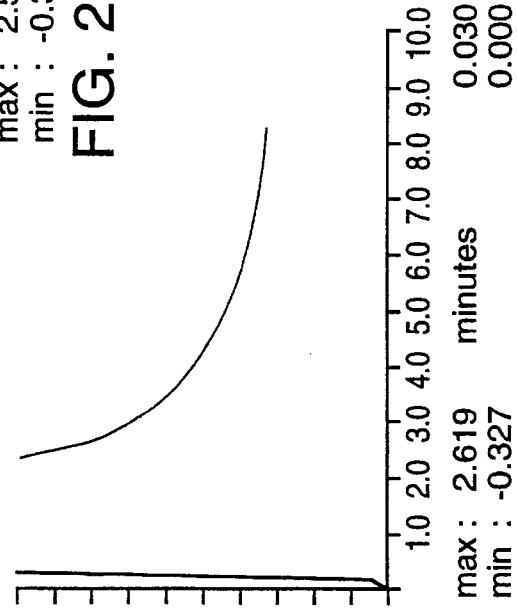
Figure 2A:
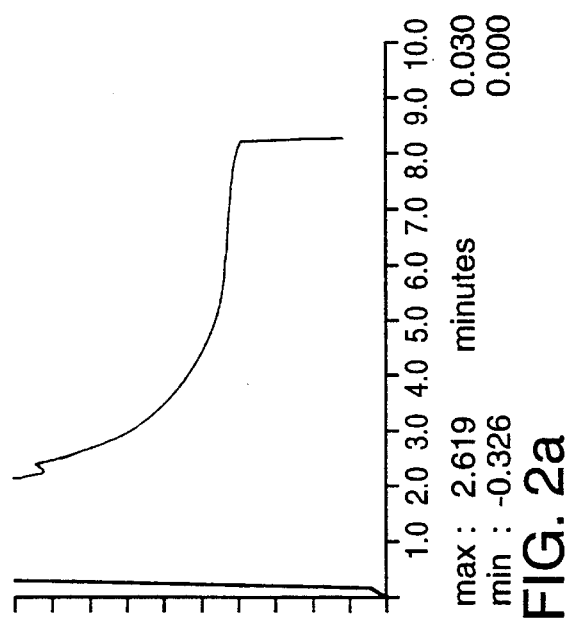

The above-mentioned term "optionally saturated and/or heterogeneous ring system of five or six members" refers to a hydrocarbon ring of five or six atoms which has 0, 1 or 2 ethenically unsaturated bonds in the ring;

0, 1 or 2 heterogeneous atoms in the ring selected from the group consisting of N and O; and which may be substituted by halogen atoms and/or groups containing carbon, nitrogen, sulphur, oxygen and/or halogen atoms.

The method according to the invention can be subdivided into two stages:

a) the preparation of the cysteine conjugate; and b) the splitting of said cysteine conjugate into, inter alia, the thiol compound(s) concerned.

The preparation of the cysteine conjugate is carried out by the addition reaction of cysteine with a compound having the formula $(R_1)(R_2)C=C(R_3)$—CO—$R_4$ in which the symbols $R_1$, $R_2$, $R_3$ and $R_4$ generally represent a hydrogen atom, an alkyl group containing 1–5 carbon atoms, an alkylene group containing 2–6 carbon atoms, a cycloalkyl or cycloalkenyl group containing 5–10 carbon atoms or an aryl group containing 6–10 carbon atoms, which abovementioned groups may be substituted by halogen atoms and/or one or more groups containing carbon, nitrogen, sulphur, oxygen and/or halogen atoms. Preferably either the groups $R_2$ and $R_4$ represent hydrogen or an alkyl group containing 1–3 carbon atoms and the combination of $R_1$ and $R_3$ represents, together with the carbon atoms to which the groups are bound, an optionally saturated and/or heterogeneous ring of five of six members (i.e. the carbon atom of the —CO— group is not a ring member), or the groups $R_1$ and $R_3$ represent a hydrogen atom or an alkyl group containing 1–3 carbon atoms and the combination of $R_1$ and $R_4$ an optionally saturated and/or heterogeneous hydrocarbon ring of five of six members (i.e. the carbon atom of the CO-group is a ring member), or the groups $R_1$ and $R_2$ represent a hydrogen atom or an alkyl group containing 1–3 carbon atoms and the combination of $R_3$ and $R_4$ represents, together with the carbon atoms to which the groups are bound, an optionally saturated and/or heterogeneous hydrocarbon ring of five or six members (i.e. the carbon atom of the CO-group is a ring member).

Examples of suitable starting compounds for the method according to the invention are the following:

furfural having the formula

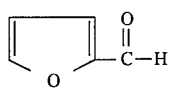

α-ionone having the formula

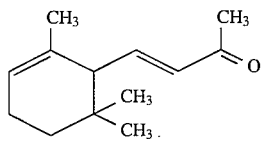

pulegone having the formula

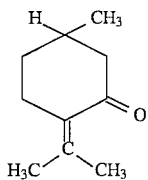

carvone having the formula

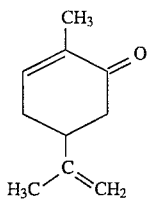

carvenone having the formula

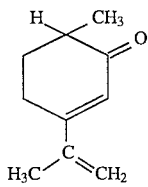

ferulic acid having the formula

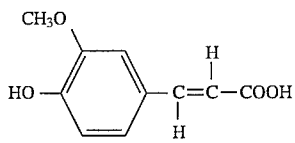

the methylester of cinnamic acid having the formula

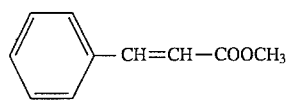

5-methoxyfuranon having the formula

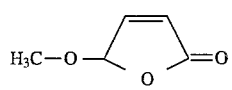

the methylester of ferulic acid having the formula

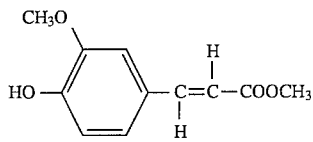

mesityloxide having the formula $(CH_3)_2-C=CH-CO-CH_3$ and citral having the formula $(CH_3)_2C=CH-(CH_2)_2-(CH_3)C=CH-CHO$.

The resulting products from the above-described starting compounds have flavoring properties.

Further representatives of suitable starting compounds are unsaturated sugars having the formula

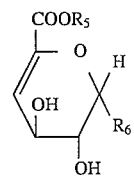

in which the symbol $R_5$ represents a hydrogen atom, an alkyl group containing 1–24 carbon atoms or an alkaline ion (e.g., alkali metal ion, such as sodium, potassium, and lithium) and $R_6$ represents a group consisting of 1–7 monosaccharides selected from the group consisting of glucose, mannose, galactose, arabinose, fucose, xylose, rhamnose, uronic acids and derivatives thereof (such as the acetates, pyruvates, amines and sulphates which are also suitable as starting compounds for the method according to the invention). Preferably $R_6$ represents a glucose-rhamnose-glucose group. The cysteine-conjugates obtained in the first stages of the invention are simply convertable in the second stage of the invention into compounds with the formula

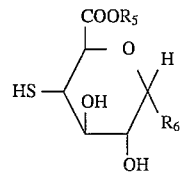

having flavouring properties.

Many types of cysteine conjugates are known as such from the prior art. For example, the preparation of a cysteine conjugate is known from Applied and Environmental Microbiology, May 1985, pages 1146–1153. In this reference, 16-dehydroprogesterone is converted with L-cysteine in a non-enzymatical manner into 16-S-cysteinyl-progesterone. Surprisingly, by means of a second stage the cysteine conjugate can be converted in the presence of a β-lyase into 16-mercaptoprogesterone. The diagram below illustrates the synthesis route described above:

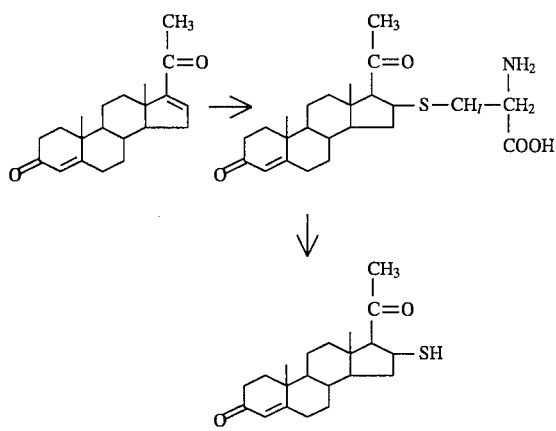

The thiol steroid shown above has specific pharmacological properties.

Reference may be made to the following additional references relating to specific cysteine conjugates or derivatives derived therefrom:

1) J. Chem. Soc. Chem. Commun. 1986, pp. 1331–1333;
2) Journal of Food Science, vol. 51, no. 5, 1986, pp. 1191–1194;
3) Planta (1986) 169: 208–215; and
4) Carbohydrate Research 142 (1985), pp. 93–105.

The cysteine used in the method according to the present invention has the formula $HS-CH_2-CH(NH_2)-COOH$. In view of the spectrum of activity of the β-lyase to be used in the method according to the present invention, L-cysteine is used.

The β-lyase (synonymous to the terms "C—S-lyase" and "cysteine conjugate β-lyase") to be used in the method according to the present invention is an enzyme dependent on a pyridoxal 5-phosphate (vitamin B6). In addition to being present in a large number of intestinal bacteria (in 24 out of the 43 arbitrarily chosen intestinal bacteria investigated, indicating a general distribution of β-lyase among gastrointestinal bacteria), the β-lyase is also present in some vegetable and animal cells (Larsen G. L., "Distribution of cysteine conjugate β-lyase in gastro-intestinal bacteria and the environment, Xenobiotica (1985), Volume 15, pages 199–209). The bacterial β-lyases are able to convert a wide spectrum of substrates, in particular both S-alkyl- and S-arylcysteine conjugates, whereas the spectrum of activity of β-lyases of vegetable or animal origin is limited. Measured with the cysteine-propachlor conjugate (an β-alkylcysteine conjugate), the β-lyase originating from the anaerobic intestinal bacterium *Eubacterium limosum* is the most active enzyme and has the lowest substrate specificity (Larsen, loc. cit.). If, however, the conversion of S-(2-benzothiazolyl)cysteine (an S-arylcysteine conjugate) is examined, it emerges that the β-lyase from an anaerobic Fusobacterium species has virtually an identical activity. β-lyase from *F. necrophorum* and *E. limosum* differ not only in substrate specificity, but also in size, namely 228 kd and 75 kd (2×38 kd) respectively and also in stability. The enzyme from *F. necrophorum* requires pyridoxal 5-phosphate for stability but is then also more stable to heat. β-lyases from *E. limosum* and *F. varium* exhibit no activity with D-cysteine conjugates and have, in general, a lower activity for S-alkylcysteine conjugates than for the S-arylcysteine conjugates.

The isolation of β-lyase from both *E. limosum* and *F. varium* does not have to be carried out under anaerobic conditions. This indicates that the enzyme is not sensitive to oxygen. It also emerges from the isolation method that the enzyme is located in the cell. The second step described above of the method according to the present invention can therefore be carried out with purified/extracted β-lyase or, if the substrates are absorbed by the bacterial cells and are converted therein, with the respective bacteria themselves.

On page 208 of Larsen (loc.cit.) the following sentence is mentioned: "These studies have shown the general distribution of β-lyase in the gastrointestinal bacteria and its presence in anaerobic and aerobic bacteria in the environment", so any man skilled in the art would be able to easily isolate bacteria containing a β-lyase.

Further to the above bacteria, other bacteria containing β-lyase are suitable for the method according to the invention (e.g., *Escherichia coli*, *Salmonella typhimurium*, *Enterobacter cloacae*, *Bacillus brevis*, *Pseudomonas taetrolens*, *Pseudomonas aromatica* and *Pseudomonas fluorescens*). Strains of bacteria capable of producing β-lyase can be easily selected by a simple search (e.g., via a computer data base of scientific literature) of articles dealing wtih xenobiotica as well as articles concerning bacterials strains having either β-lyase, C—S lyase, or cysteine-desulfhydrase activity.

Several other conversions of cysteine conjugates by means of β-lyase are known from the prior art. For instance, in Larsen G. L. et al., Molecular Pharmacology (1986) Volume 29, pages 97–103, β-lyases from gastrointestinal bacteria like the bacterium *Eubacterium limosum* were found to cleave the thioether linkage of S-alkyl- and S-aryl-L-cysteine conjugates. These cysteine conjugates were used in an amount of 2–0.01 μmol (see Table 2 of the above reference). More in particular, these conjugates were: (1) the cysteine conjugate of 2-S-cysteinyl-N-isopropylacetanilide (=propachlor cysteine conjugate); (2) the S-oxide of the cysteine conjugate of propachlor; (3) trans-9-hydroxy-10 (S-(L-cysteinyl))-9,10-dihydrophenanthrene; (4) S-benzyl-L-(N-acetyl)cysteine; (5) S-1,2-dichlorovinyl-D-cysteine; (6) S-1,2-dichlorovinyl-L-cysteine; (7) S-(2-benzothiazolyl)-cysteine; (8) S-benzyl-L-cysteine; (9) S-benzyl-D-cysteine; (10) S-ethyl-L-cysteine and (11) S-ethyl-D-cysteine. However, none of the above mentioned cysteine conjugates were prepared by the conversion of cysteine with a starting compound having a —C=C—CO-moiety which is a prerequisite for the starting compounds used in the process according to the present invention. On account of this —C=C—CO-moiety it is possible to obtain a high yield of the resulting thiol product (see for instance Example I below) which is very important for a process to be successful on a commercial scale.

In Larsen G. L. et al., Xenobiotica (1983), vol. 13, no. 11, pages 689–700, the β-lyase from the gastrointestinal bacterium *Fusobacterium necrophorum* was found to cleave the thioether linkage of both S-alkyl- and S-aryl cysteine conjugates. More in particular these conjugates were: (1) 2-S-cysteinyl-N-isopropylacetanilide (=propachlor-cysteine conjugate); (2) 1,2-dihydro-1-hydroxy-2-S-cysteinylnaphthalene; (3) 2,4-dinitro-1-S-cysteinyl benzene; (4) S-(2-benzothiazolyl)cysteine; and (5) S-methyl cysteine; see Table 3 on page 698 of this reference. However, none of the above mentioned cysteine conjugates were prepared by means of the reaction of cysteine with a starting compound having a —C=C—CO—moiety as required according to the invention.

Referring to Lamoureux et al. (loc.cit.), it is brought to the fore that the cysteine conjugates disclosed therein, i.e. S-(penta-chlorophenyl)cysteine and S-(2,4-dinitrophenyl- )cysteine, were not prepared by a reaction between cysteine and a starting compound having a —C=C—CO-moiety (which is a prerequisite for the invention).

Hansen S. E. et al., C. R. Trav. Lab. Carlsberg, Ser. Chim. (1959), Vol. 31, page 193 refers to a continuous chromogenic method for the assay of C—S-lyases (=β-lyases) with S-(2,4-dinitrophenyl)-L-cysteine as substrate. In this respect it is remarked that this substrate is not the product of an addition reaction between cysteine and a starting compound having a —C=C—CO—moiety as required according to the present invention.

U.S. Pat. No. 4,328,311 (Rowley, G. L.) discloses methods and compositions for conjugating a polyfunctional compound having a plurality of reactive primary and/or secondary amino functionalities with a second compound having a mercapto functionality, usually polyfunctional, having functionalities reactive to acyl groups (e.g., hydroxylic and amino). The polyamino compound is initially reacted with a linking compound having an active halogen or pseudohalogen and a non-oxo carbonyl functionality for reacting with at least one of the amino functionalities. The mercapto compound is then added to the halo or pseudohalo containing polyamino compound for substitution of the halo atoms to provide a thioether linked conjugate of the mercapto group with the polyamino compound. In this respect it is stated that according to the present invention the mercapto compound cysteine is bound via an addition reaction to the starting compounds having a —C=C—CO-moiety, i.e., the starting compounds used in the first stage of the method according to the present invention differ from the starting compounds according to Rowley.

Kitazume T. et al., J. Chem. Soc. Chem. Commun. (1986), pages 1331–1333 discloses an enzyme assisted Michael addition to introduce a centre of chirality into fluoro compounds. Pig liver esterase can be utilized in the addition reaction of 2-(trifluoro methyl)propenic acid with 2-aminophenol, 2-aminothiophenol, o-phenylene diamine and 4-methyl-2-aminophenol. However, the first stage of the method according to the invention is defined by both the use of cysteine as the mercapto compound and its non-enzymatical character.

In view of the industrial scale on which the method according to the present invention is to be carried out, the starting concentration of the cysteine conjugate (which is converted by the microbial β-lyase in the second stage of the method or the present invention) should be as high as possible, at least ≧1 mM and preferably in a range of 1.5–50 mM. The upper limit of the concentration of the cysteine conjugate depends on several parameters (e.g., the amount of microorganisms used (expressed as optical density), the particular microorganism used, etc). As the end product of the method of the present invention is a thiol product, it is surprising that in spite of the generally known toxic properties of thiols for microorganisms the method of the present invention was still applicable. In this respect it is brought to the fore that thiols are toxic on account of their ability to form reactive compounds with macromolecules. Such macromolecules are present in the cell and cell membrane of bacteria. Therefore it is to be expected that thiols are toxic for bacteria. For supporting this general property of thiols, see the following references indicating the toxicity of thiols:

(1) Chen et al (1990), Journal of Biological Chemistry, vol. 265, no. 35, page 21603: "The cysteine conjugates are cleaved to yield ammonia, pyruvate, and an electrophilic thiol containing fragment. This reaction is catalyzed in renal epithelial cells by the enzyme 'cysteine conjugate β-lyase'. The reactive thiol fragment binds to cellular macromolecules to initiate cellular damage. The loss of cell viability correlates with the amount of reactive fragment which binds to cellular macromolecules."; and (2) Tomisawa et al., (1986), Biochemical Journal, vol. 235, page 569: "Thus, from a toxicological point of view, the thiol compounds generated by the action of 'cysteine-conjugate β-lyase' are of great importance. The thiol compounds are highly reactive and become covalently bound to cellular macromolecules to cause cell injury."

The method according to the present invention results in many types of thiol compounds with divergent applications. Examples of substances to be prepared pertain to the field of perfumes and flavourings (p-mentha-8-thiol-3-one, furfurylmercaptan damascone derivatives), pharmacological steroid compounds, and repellants (Warburganal).

Preferably, bacterial cells are utilizied instead of purified β-lyase. The process using purified β-lyase is much more laborious since the enzyme must be removed from the cell, the stability of the enzyme is questionable, the enzyme normally needs a co-factor, and the separation of the thiol product is more difficult.

The invention is explained on the basis of the examples below; these examples should not be interpreted as restrictive. All the strains mentioned in the examples below are freely available for the public with the exception of the strain of *Pseudomonas fluorescens*.

EXAMPLES

Example I

In this example, the starting compound is pulegone, which is converted via S-cysteinyl-pulegone into p-mentha-8-thiol-3-one. This preparation is illustrated in the diagram below:

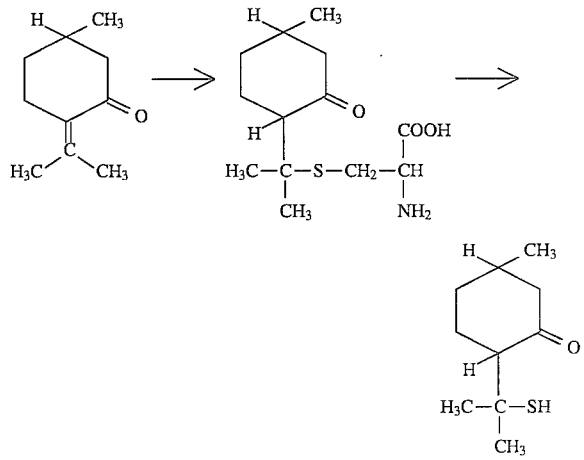

Stage 1) Preparation of S-cysteinyl-pulegone.

12.2 g of L-cysteine (0.1 mol) (high purity analytical grade supplied by Fluka A. G.), 16.3 ml of pulegone (0.1 mol) and 2.0 g of KHCO₃ (0.02 mol) were stirred for 22 hours in 100 ml of H₂O at room temperature. The yoghurt-like mixture, which was no longer stirrable, was then allowed to stand for 3 days. The product obtained was then filtered off by suction and washed respectively with 100 ml and 2×50 ml of H₂O. After drying over CaCl₂ in vacuo, the product was washed with acetone. The yield was 17.9 g (0.066 mol). Appendix 1 shows the 90 MHz H-NMR spectrum of the product obtained.

More particularly, an elementary analysis of the product purified by thin-layer chromatography clearly indicates a 1:1 reaction product.

| Elementary analysis (carried out in duplicate). | |
|---|---|
| Actual: | Calculated (substance + 1/2 mol of $H_2O$) |
| % C: 54.76 | 55.29 |
| % H: 8.36 | 8.57 |
| % N: 5.01 | 4.96 |
| % O: 19.60 | 19.83 |
| % S: 11.13 | 11.35 |

Stage 2) Splitting of the S-cysteinyl-pulegone by a β-lyase.

The organism used in this stage was Eubacterium limosum ATCC No. 10825. Said organism was cultured under anaerobic conditions at 37° C. on a P-medium which had the composition below:

| Composition of P-medium: | |
|---|---|
| Casein peptone (Difco) | 10 g/l |
| Beef extract (Difco) | 3 g/l |
| Yeast extract (Difco) | 3 g/l |
| Glucose (Merck) | 2 g/l |
| Tween 80 (Serva) | 1 g/l |
| Cysteine-HCl (Fluka) | 0.5 g/l |
| Resazurin (Serva) | 0.25 g/l |
| Salt solution (analytical grade) | 40 ml/l |
| Final pH: 7.2 | |
| The salt solution consisted of: | |
| $CaCl_2$ | 0.2 g/l |
| $MgSO_4.7H_2O$ | 0.2 g/l |
| $K_2PO_4$ | 1.0 g/l |
| $KH_2PO_4$ | 1.0 g/l |
| $NaHCO_3$ | 10.0 g/l |
| NaCl | 2.0 g/l |

The cell material for producing β-lyase was obtained by culturing *E. limosum* (3% inoculation) on the abovementioned P-medium in serum bottles having a capacity of 300 ml. By filling the bottle with P-medium to a few centimeters below the rim, the medium became sufficiently low in oxygen as a result of sterilization to make growth of *E. limosum* possible. After an incubation time of 1 day at 37° C., the cells were harvested by centrifuging them at 50,000 x g for 20 minutes. The cells were subsequently washed twice with a buffer having a pH of 7 which contained 50 mM of phosphate and 50 mM of pyridoxal-HCl. The pellet (approx. 1 g wet weight from 300 ml) was taken up in 10 ml of buffer.

S-cysteinyl-pulegone (0.3 g/l=1.1 mM) was converted in the buffer with the concentrated cell suspension of *E. limosum* described above (final concentration: 1.6 mg dry weight/ml). The reaction was carried out for 1 hour at 30° C. and was terminated by centrifuging the reaction mixture for 5 minutes at 11,000 x g.

As a control, two tests were carried out:

a) As a control, boiled cells (denatured enzymes) were used in the test described above.

b) In order to be able to assess whether the SH product (p-mentha-8-thiol-3-one) had converted by the S-methyl transferase into the S-methyl product (p-mentha-8-thiomethyl-3-one), the cells were also incubated with p-mentha-8-thiol-3-one.

The results of gas chromatography analysis of this example (sample no. 1) and the two control tests (samples 2 and 3) are shown in Appendix 2.

To carry out the abovementioned gas chromatographic analysis, 1 part of chloroform ($CHCl_3$) was mixed with 1 part of the reaction mixture described above. 1 μl of this extract was injected into a gas chromatograph having a 20M carbowax column (1.3 m RVS, column temperature: 145° C., injection port and TCD temperature: 160° C.).

Example II

The method according to Example I was repeated, but with the difference that instead of being carried out on a 1 ml scale, the test was carried out on a 10 ml scale. In this test, the cells were used in a double concentration (viz. 3.2 mg dry weight/ml) and the incubation was carried out for 3 hours at 37° C. For a gas chromatographic analysis, a sample (sample B) was taken from this in the following manner.

One part of dichloromethane ($CH_2Cl_2$) was mixed with 4 parts of the reaction mixture. 0.4 μl of this extract was injected into a Varian gas chromatograph in which a 10% FFAP-chromosorb was provided in a WAW column (2 m RVS, i.d. ⅛") (column temperature: 160° C.; injection port and FID temperature: 180° C.).

As a comparison, in addition to the gas chromatogram of sample B shown in Appendix 3 as a control, the gas chromatograms of a) p-mentha-8-thiol-3-one, b) p-mentha-8-thiomethyl-3-one, c) pulegone, and d) S-cysteinyl-pulegone were recorded without cells being used at the same time.

Figure 3A:
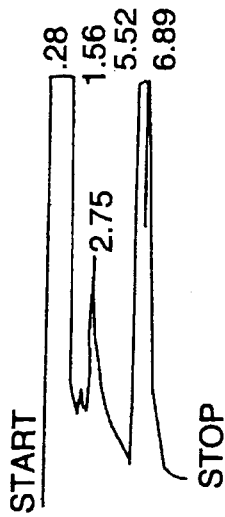
FIG. 3 shows gas chromatography analysis of some extracts of Example II.
Figure 3B:
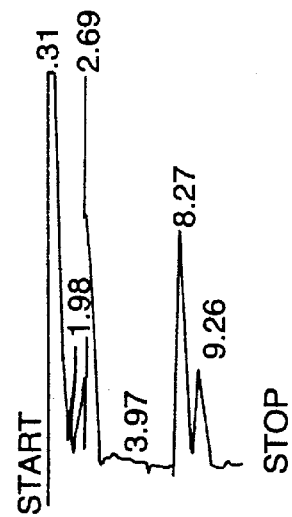
Figure 3C:
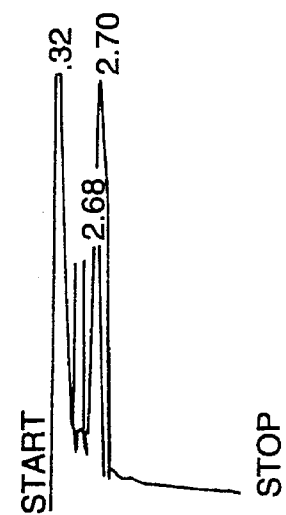
Figure 3D:
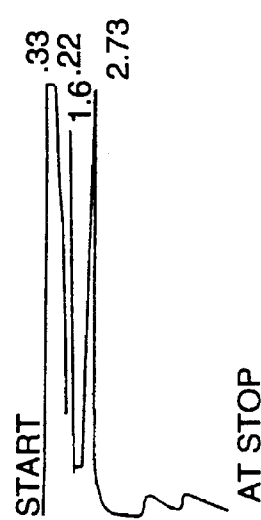
Figure 3E:
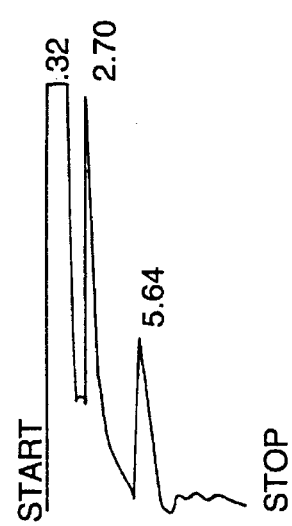
Figure 4:
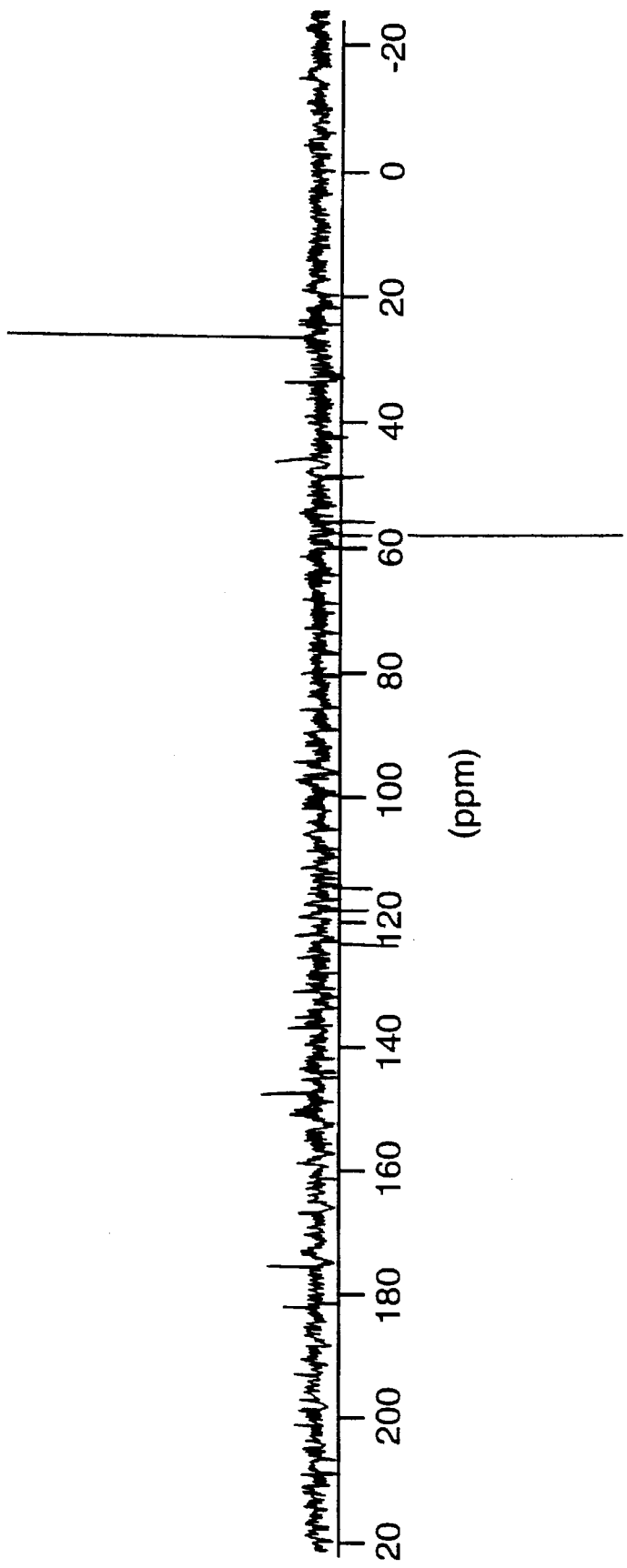
FIG. 4 shows the NMR spectrum of the cysteine conjugate of ferulic acid obtained according to Example VI.
Figure 5:
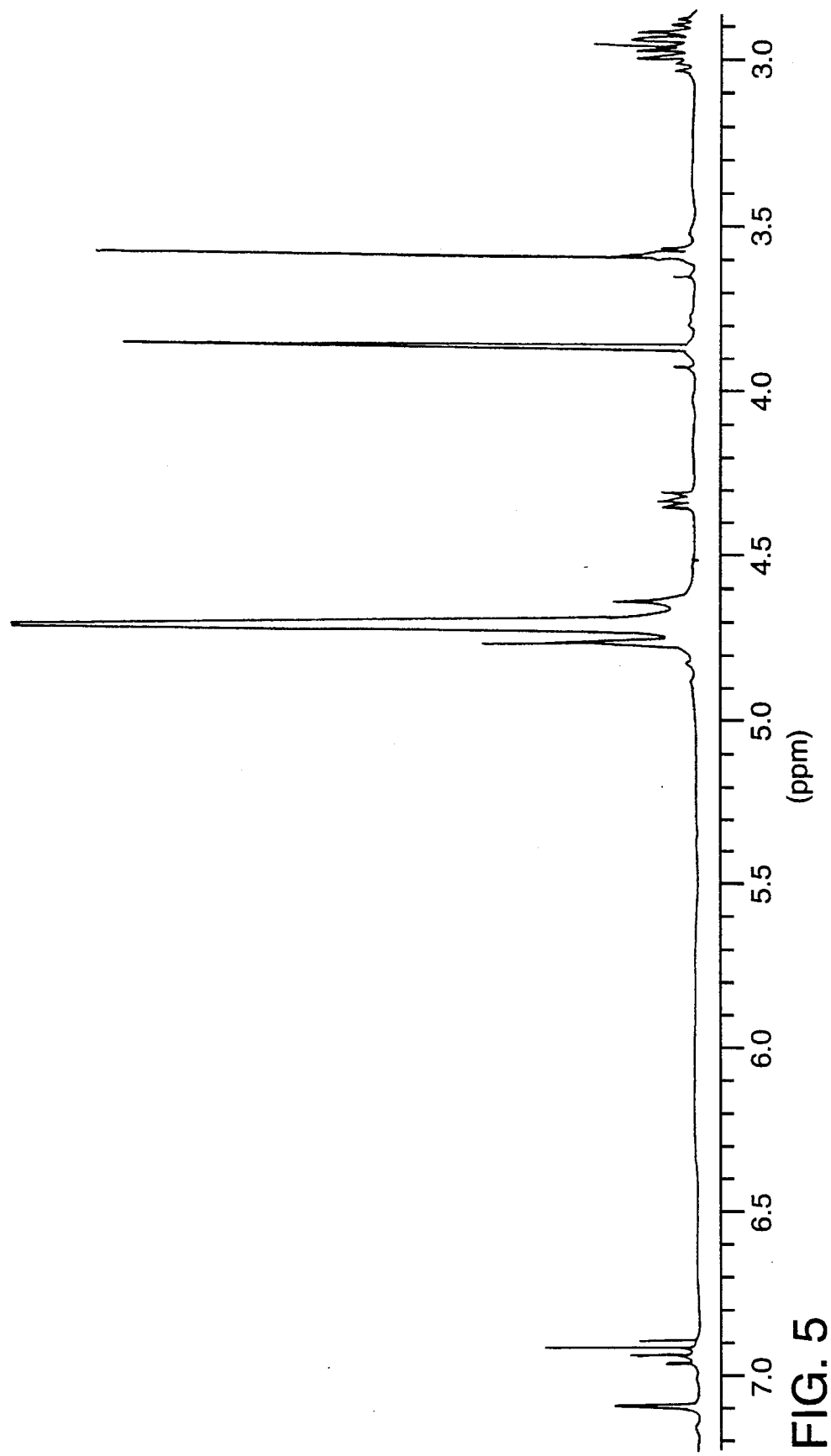
FIG. 5 shows the NMR spectrum of the cysteine conjugate of the methylester of ferulic acid obtained according to Example VI.
Figure 6:
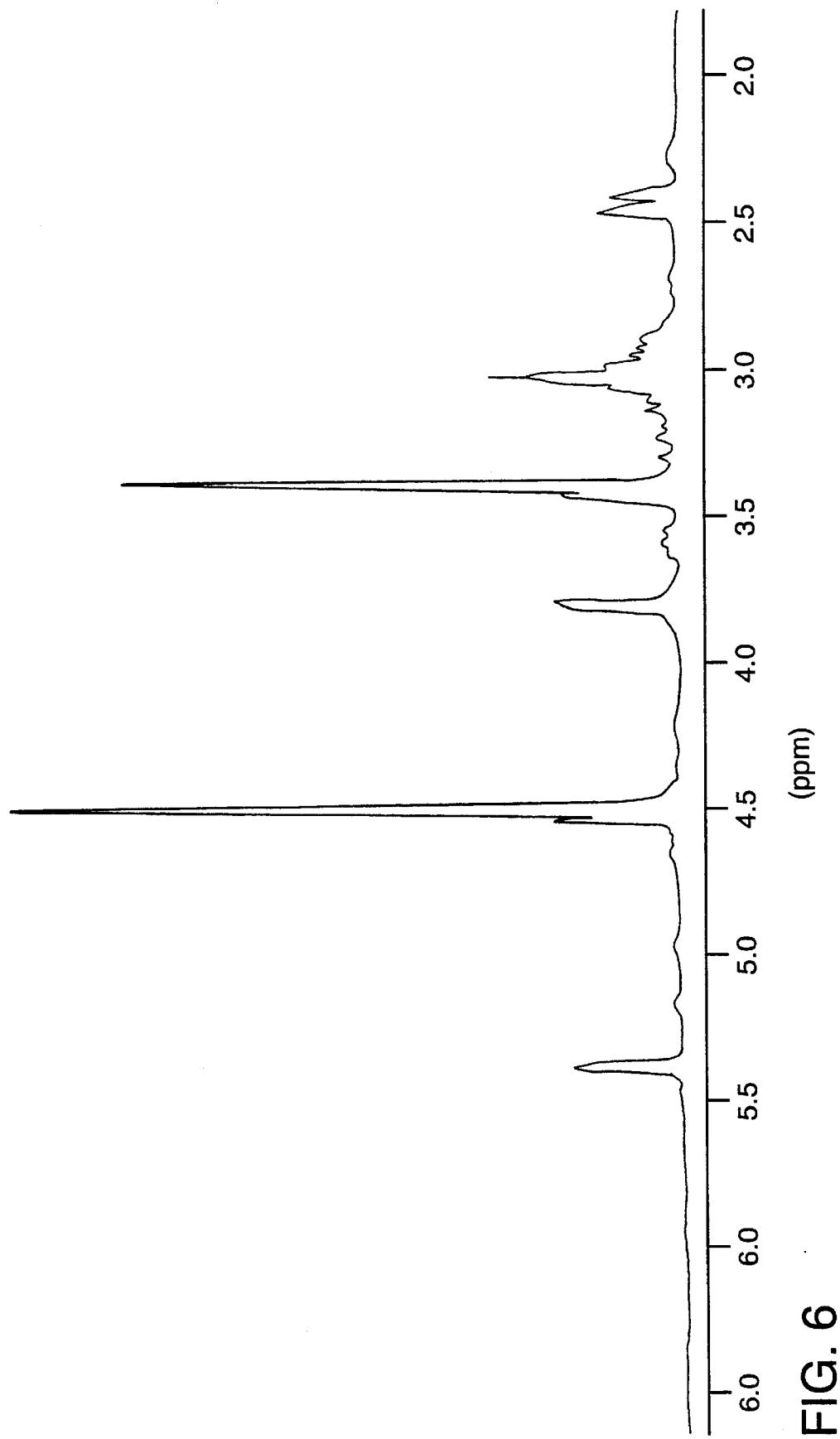
FIG. 6 shows the NMR spectrum of the cysteine conjugate of the 5-methoxyfuranon obtained according to Example VI.
Figure 7:
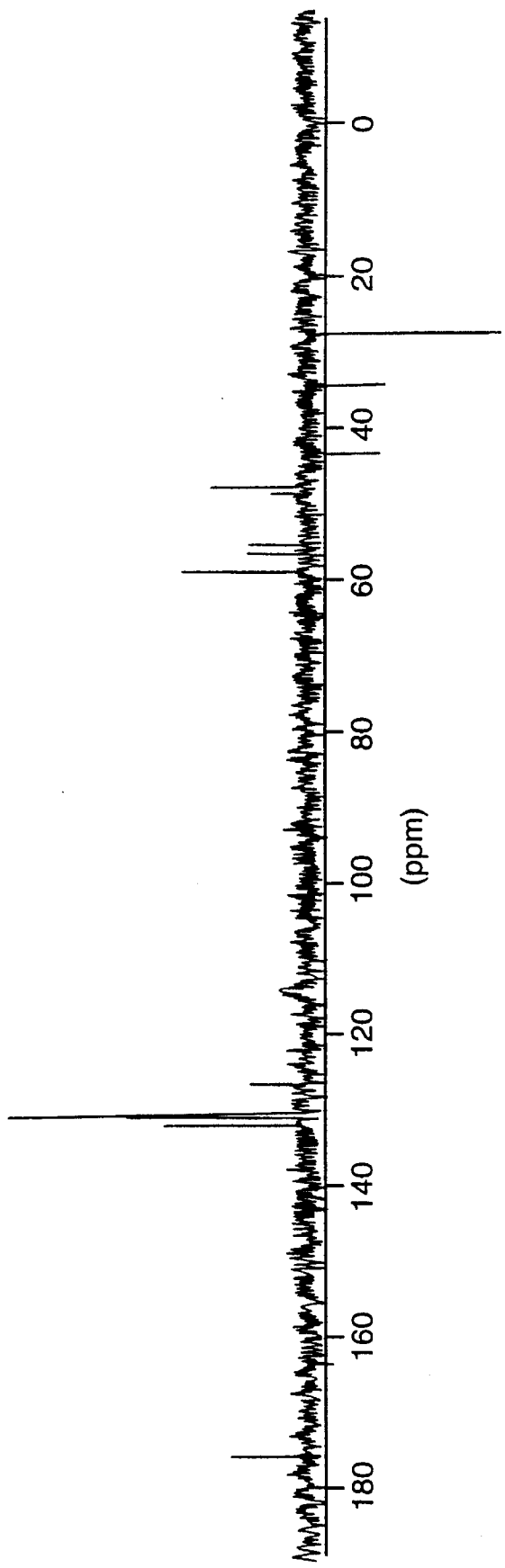
FIG. 7 shows the NMR spectrum of the cysteine conjugate of the methylester of cinnamic acid obtained according to Example VI.

It follows from the chromatograms shown in Appendix 3, inter alia, that no detectable p-mentha-8-thiomethyl-3-one is formed (compare 3b with 3e). The pulegone peak in FIGS. 3*d* and 3*e* (retention time 2.7 min.) may be explained by the fact that some of the S-cysteinyl-pulegone dissolves in the extraction agent and is decomposed in the gas chromatograph (160° C.).

The chromatogram of chemically synthesized p-mentha-8-thiol-3-one (FIG. 3*a*) reveals an L- and D- stereoisomer ratio of approximately 2:1. The biologically prepared p-mentha-8-thiol-3-one (FIG. 3*e*) has a completely different ratio of the two isomers which is approximately 9:1.

Example III

In this example the starting compound is furfural which is converted via S-cysteinyl-furfural into the thiol derivative furfurylmercaptan.

Stage 1): Preparation of a conjugate of furfural and cysteine.

1300 g of cysteine-HCl was dissolved in 26 l 50% ethanol. To this solution, 780 g potassium acetate was added under stirring. After the mixture was stirred to clarity, 904.8 g furfural was added. A yellow precipitate was formed after 15 minutes. The mixture was stirred for 4 hours at room temperature and stored for 12 hours at 5° C. The precipitate was purified by filtration and washing (3 times) with 10 l 50% ethanol. The structure of the dried conjugate was confirmed by its melting point (127° C.) and 400 MHz NMR analysis. The purity of the conjugate was about 99%. The yield of the conjugate prepared by this process was 77.8%, based on theoretical yield.

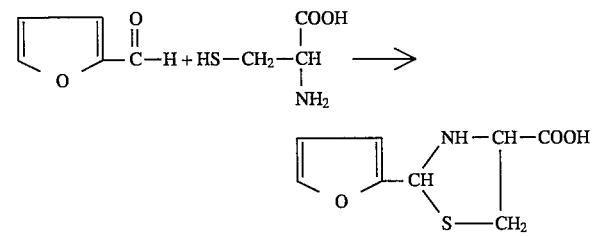

Stage 2): Splitting of the furfuryl-cysteine conjugate (MW= 235).

0.6 g/l (3 mM) of the furfural-cysteine conjugate obtained in stage (1) was dissolved in a 50 mM potassium phosphate buffer pH 6.5, containing *Enterobacter cloacae* NCIMB 10101, cells resuspended to an optical density at 535 nm of 4. Previously, these cells were grown overnight at 30° C. in nutrient broth no. 2 medium (Oxoid Ltd., Basingstoke, England), harvested by centrifugation and washed with potassium phosphate buffer pH 6.5.

After incubation of the cell suspension with the furfural cysteine conjugate for 24 hours at 30° C., the content of the thiol end product furfurylmercaptan was determined. For this purpose, the furfurylmercaptan was extracted from a 10 ml sample with a Sep-Pak C18 column (Millipore Corporation, Milford, Mass.) and eluted with 2 ml of dichloromethane. 1 µl of the dichloromethane solution was injected on a gas chromatographic column containing a fused silica column. Thus it was concluded that 120 mg/l (1.05 mM) of furfurylmercaptan had been formed by biocatalytic activity. Without cells, no furfurylmercaptan was produced.

Microbial conversion of the furfural-cysteine conjugate in a concentration of 22 mM and in the presence of a microorganism content corresponding to an optical density (OD) at 535 mm of 8 can be excellently performed; whereas the conversion at a concentration of 33 mM is diminshed. The diminished conversion might be circumvented by using an increased microbial content.

Example IV

In addition to the microorganism *Enterobacter cloacae* NCIMB 10101 utilized in Example III, other microorganisms have been used for the conversion of the furfuralcysteine conjugate obtained in stage (1) of Example III into furfurylmercaptan. The microorganisms in question were grown overnight in the media and at temperatures mentioned in Table 1. The cells were harvested by centrifugation and washed with potassium phosphate buffer pH 7, containing 50 µm pyridoxal-HCl. Cell suspensions were made by resuspending the cells in the buffer to an optical density at 535 nm of 4.

The cell suspensions were incubated with 0.3 g/l (1.5 mM) of the furfural-cysteine conjugate at temperatures mentioned in Table 1. The furfurylmercaptan content was determined in the above described way. The results are given in Table 1.

TABLE 1

| Microorganism | growth medium | growth temp.(°C.) | incubation temp.(°C.) | furf.mer. (mg/l) | furf.mer (mM) |
|---|---|---|---|---|---|
| *Enbacterium limosum* ATCC 10825 | P | 37 | 30 | 7.7 | 0.067 |
| *Escherichia coli* ATCC 4157 | NB | 37 | 30 | 20.1 | 0.176 |
| *Fusobacterium varium* ATCC 85010 | CMM | 35 | 35 | 0.5 | 0.004 |
| *Salmonella typhimurium* TA 98 | NBR | 37 | 37 | 13.5 | 0.118 |
| *Salmonella typhimurium* TA 100 | NBR | 37 | 37 | 20.4 | 0.179 |
| *Salmonella typhimurium* TA 102 | NBR | 37 | 30 | 31.2 | 0.273 |
| *Enterobacter cloacae* NCIMB 8151 | NB | 30 | 30 | 28.3 | 0.248 |
| *Fusobacterium nucleatum* ATCC 25586 | PYG | 35 | 35 | 29.9 | 0.262 |
| *Bacillus brevis* NCIMB 9372 | NB | 30 | 30 | 4.4 | 0.039 |
| *Pseudomonas taetrolens* ATCC 4683 | NB | 26 | 26 | 3.6 | 0.032 |
| *Pseudomonas aromatica* NCIMB 9043 | NB | 26 | 26 | 0.5 | 0.004 |
| *Pseudomonas fluorescens* (collection of Applicant) | NB | 26 | 30 | 3.6 | 0.032 |

Definition of the media
a) P = P-medium*
b) NB = Nutrient broth no.2 (Oxoid LTD)
c) CMM = Chopped Meat Medium (ATCC 593)**
d) NBR = Rich Nutrient Broth Medium: per liter 25 g nutrient broth no.2
   5 g yeast extract and 5 g NaCl
e) PYG = 1% peptone, 1% yeast extract, 1% glucose and 0,5 g/l cysteine-HCl
*P-medium; DSM Catalogue of Strains 1989, 4th Ed., page 288, medium 104
**CMM ATCC Catalogue of Bacteria & Bacteriophages 1989, 17th Ed., page 313, medium 593.

Example V

Example for the preparation of a conjugate of cysteine with an unsaturated sugar and the subsequent converse on of the conjugate into the thiol compound.

Stage 1): 264.9 mg of the unsaturated tetrasaccharide having the structural formula indicated below, 62 mg of L-cysteine and 29.2 mg of $KHCO_3$ were stirred for 5 days under nitrogen in 5 ml demineralized water at room temperature. The solid white product of the reaction was collected by centrifugation. The pellet was washed twice with water (distilled three times). The structure of the conjugate product was confirmed by 60 MHz $^1$H-NMR and $^{13}$C-NMR. The yield of the conjugate-product was 72%.

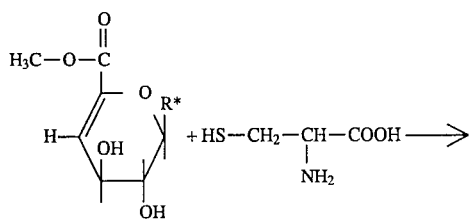

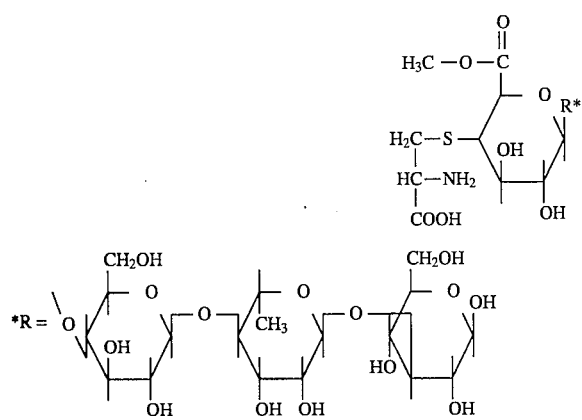

Stage 2): The conjugate-product obtained in stage (1) was converted into the corresponding thiol compound in a similar manner as described in Example IV using *Eubacterium limosum* ATCC 10825. The compound having the formula

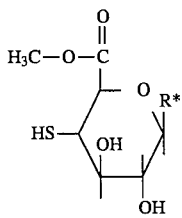

was obtained, having a specific odor reminiscent of coffee and meat.

Example VI

This example has been carried out for demonstrating the applicability of the process according to the invention for compounds having a —C=C—CO— moiety in their structure.

The compounds used as starting agent were
1) ferulic acid having the formula

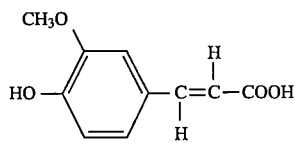

2) the methylester of ferulic acid having the formula

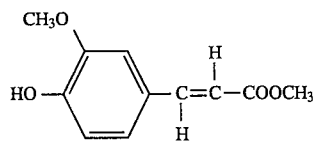

3) carvone having the formula

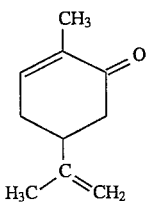

4) 5-methoxyfuranon having the formula

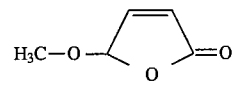

5) the methylester of cinnamic acid having the formula

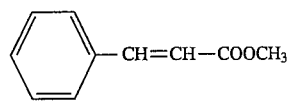

6) mesityloxide having the formula $(CH_3)_2$—C=CH—CO—$CH_3$.

The method was carried out in accordance with Example II with the help of the bacterium *Eubacterium limosum* ATCC 10825. NMR spectra of the cysteine conjugates of ferulic acid, the methylester of ferulic acid, 5-methoxyfuranon and the methylester of cinnamic acid are illustrated in FIGS. 4–7 (Appendices 4–7) respectively. All the thiol compounds obtained had a specific odor (the cysteine conjugates obtained after the first stage were odorless):

(1) beef tea odor with a cauliflower note;
(2) beef tea odor with a cauliflower note;
(3) herby odor;
(4) bread crust odor;
(5) fruity odor (in particular an odor reminiscent of grapefruit, pear and apple) and a meat note; and
(6) odor of black current (cassis).

Example VII

A commercial cocoa mix was used to prepare two different batches of beverage. The first batch is evaluated without any further addition while p-mentha-8-thiol-3-one prepared according to Example II was added to the second batch in the ratio of 20 μg of said p-mentha-8-thiol-3-one to each kilo of cocoa beverage. The beverage containing p-mentha-8-thiol-3-one has a fuller and richer flavour comparing to the beverage without p-mentha-8-thiol-3-one.

We claim:

1. A method for preparing thiol compounds, comprising:
   (1) reacting cysteine by a non-enzymatical addition reaction with a compound having the formula $(R_1)(R_2)C=C(R_3)$—CO—$R_4$ via an —S— bridge to form a cysteine conjugate,
   wherein $R_1$, $R_2$ and $R_3$ are each selected from the group consisting of: hydrogen; an alkyl group containing 1–5 carbon atoms; an alkylene group containing 2–6 carbon atoms; a cycloalkyl or cycloalkenyl group containing 5–10 carbon atoms and an aryl group containing 6–10 carbon atoms; and $R_4$ is selected from the group consisting of: hydrogen; an alkyl group containing 1–5 carbon atoms; an alkylene group containing 2–6 carbon atoms; a cycloalkyl or cycloalkenyl group containing 5–10 carbon atoms; an aryl group containing 6–10 carbon atoms; —OH and —$OCH_3$, or wherein a combination of two groups selected from the group consisting of $R_1$, $R_3$ and $R_4$, together with the carbon atoms to which the groups are bonded, form a ring system of five or six members, wherein said ring has 0–3 ethenically unsaturated bonds and wherein said ring has 0–2 heterogeneous atoms selected from the group consisting of N and O, or wherein said compound having the formula $(R_1)(R_2)C=C(R_3)-CO-R_4$ is a compound having the formula:

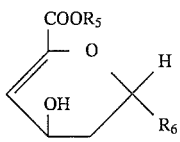

in which the $R_5$ is selected from the group consisting of hydrogen, an alkyl containing 1–24 carbon atoms and an alkaline ion, and $R_6$ is 1–7 monosaccharides and wherein said monosaccharides are selected from the group consisting of glucose, mannose, galactose, arabinose, fucose, xylose, rhamnose, uronic acid, and acetate, pyruvate, amine and sulfate derivatives thereof, and (2) reacting said cysteine conjugate in a concentration of >1 mM conjugate with a cysteine conjugate β-lyase produced by bacteria selected from the group consisting of *Eubacterium limosum*, *Escherichia coli*, *Fusobacterium varium*, *Fusobacterium nucleatum*, *Salmonella typhimurium*, *Enterobacter cloacae*, *Bacillus brevis*, *Pseudomonas taetrolens*, *Pseudomonas aromatica* and *Pseudomonas fluorescens* to form a thiol compound and recovering said thiol compound.

2. The method according to claim 1, wherein $R_2$ and $R_4$ are hydrogen or an alkyl group containing 1–3 carbon atoms and the combination of $R_1$ and $R_3$ is, together with the carbon atoms to which the groups are bound, an optionally saturated and/or heterogeneous ring of five or six members.

3. The method according to claim 2, wherein said compound having formula $(R_1)(R_2)C=C(R_3)-CO-R_4$ is furfural.

4. The method according to claim 3, wherein said thiol is furfurylmercaptan.

5. The method according to claim 1, wherein $R_2$ and $R_3$ are hydrogen or an alkyl group containing 1–3 carbon atoms and the combination of $R_1$ and $R_4$ is, together with the carbon atoms to which the groups are bound, an optionally saturated and/or heterogenous ring of five or six members.

6. The method according to claim 1, wherein $R_1$ and $R_2$ are a hydrogen atom or an alkyl group containing 1–3 carbon atoms and the combination of $R_3$ and $R_4$ is, together with the carbon atoms to which the groups are bound, an optionally saturated and/or heterogeneous ring of five or six members.

7. The method according to claim 6, wherein said compound having the formula $(R_1)(R_2)C=C(R_3)-CO-R_4$ is pulegone.

8. The method according to claim 7, wherein the thiol is p-mentha-8-thiol-3-one.

9. The method according to claim 1, wherein said cysteine conjugate has a molarity of ≧1.5 mM.

10. The method according to claim 1, wherein said compound having the formula $(R_1)(R_2)C=C(R_3)CO-R_4$ is selected from the group consisting of (a) ferulic acid having the formula

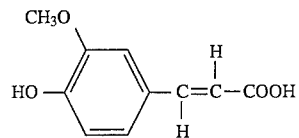

(b) the methylester of ferulic acid having the formula

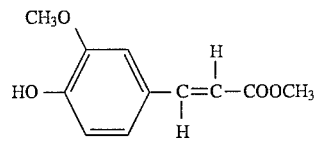

(c) carvone having the formula

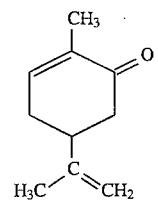

(d) 5-methoxyfuranon having the formula

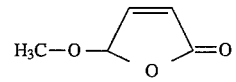

(e) the methylester of cinnamic acid having the formula

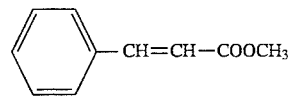

(f) mesityloxide having the formula $(CH_3)_2-C=CH-CO-CH_3$, (g) pulegone, and (h) furfural.

11. The method according to claim 10, wherein said compound having the formula $(R_1)(R_2)C=C(R_3)-CO-R_4$ is the methylester of cinnamic acid having the formula

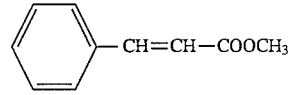

or mesityloxide having the formula $(CH_3)_2-C=CH-CO-CH_3$.

12. The method according to claim 1, wherein $R_5$ is $-CH_3$ and $R_6$ is the group having the formula

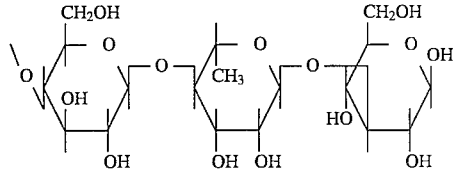

* * * * *

UNITED STATES PATENT AND TRADEMARK OFFICE
CERTIFICATE OF CORRECTION

PATENT NO. : 5,578,470

DATED : November 26, 1996

INVENTOR(S) : Antonius Kerkenaar, Diederik J. M. Schmedding and Jan Berg

It is certified that error appears in the above-indentified patent and that said Letters Patent is hereby corrected as shown below:

Title page, after 'Assignee' information, insert the following:
    --[*] Notice: The term of the patent shall not extend beyond the expiration date of Patent No. 5,182,194.--.

Column 2 Line 51 "five of six" should read --five or six--.

Column 2 Line 53 "$R_1$" should read --$R_2$--.

Column 2 Line 56 "five of six" should read --five or six--.

Column 5 Lines 49-50 "$\beta$-alkylcysteine" should read --S-alkylcysteine--.

Column 6 Line 21 "wtih" should read --with--.

Column 6 Line 22 "bacterials" should read --bacterial--.

Column 8 Line 16 "utilizied" should read --utilized--.

Column 9 Line 20 "Composltion" should read --Composition--.

Column 9 Line 32 "$K_2PO_4$" should read --$K_2HPO_4$--.

Column 11 Line 59 "Diminshed" should read --diminished--.

--continued--

UNITED STATES PATENT AND TRADEMARK OFFICE
CERTIFICATE OF CORRECTION

PATENT NO. : 5,578,470
DATED : November 26, 1996
INVENTOR(S) : Antonius Kerkenaar, Diederik J. M. Schmedding and Jan Berg It is certified that error appears in the above-indentified patent and that said Letters Patent is hereby corrected as shown below:

Column 12 Table 1, under heading 'Microorganism',
    "*Enbacterium*" should read --*Eubacterium*--.

Column 12 Table 1, under heading 'Definition of the Media',
    refer to e) "0,5" should read --0.5--.

Column 12 Line 54 "converse on" should read --conversion--.

Column 14 Line 40 "current" should read --currant--.

Claim 5 Column 15 Line 50 "heterogenous" should read
    --heterogeneous--.

Claim 10 Column 15 Line 65 "($R_3$)CO" should read --($R_3$)-CO--.

Signed and Sealed this

Twentieth Day of May, 1997

*Attest:*

*Attesting Officer*

BRUCE LEHMAN

*Commissioner of Patents and Trademarks*